US011738205B2

(12) United States Patent
Bohman et al.

(10) Patent No.: US 11,738,205 B2
(45) Date of Patent: Aug. 29, 2023

(54) LASER TREATMENT APPARATUS

(71) Applicant: JMEC CO., LTD., Tokyo (JP)

(72) Inventors: Samuel Bohman, Tokyo (JP); Hiroyuki Nishimura, Tokyo (JP); Kazuyoku Tei, Tokyo (JP)

(73) Assignee: JMEC CO., LTD., Tokyo (JP)

(*) Notice: Subject to any disclaimer, the term of this patent is extended or adjusted under 35 U.S.C. 154(b) by 149 days.

(21) Appl. No.: 16/912,964

(22) Filed: Jun. 26, 2020

(65) Prior Publication Data

US 2020/0324138 A1  Oct. 15, 2020

Related U.S. Application Data

(63) Continuation-in-part of application No. PCT/JP2018/047268, filed on Dec. 21, 2018.

(30) Foreign Application Priority Data

Dec. 26, 2017 (JP) ................. 2017-249924

(51) Int. Cl.
*A61N 5/06* (2006.01)
*A61B 18/20* (2006.01)
*A61N 5/073* (2006.01)
*A61N 5/067* (2006.01)

(52) U.S. Cl.
CPC .. *A61N 5/0616* (2013.01); *A61B 2018/20357* (2017.05); *A61N 5/067* (2021.08); *A61N 2005/0631* (2013.01); *A61N 2005/073* (2013.01)

(58) Field of Classification Search
CPC ............ A61B 18/20; A61N 5/06; A61F 9/008
See application file for complete search history.

(56) References Cited

U.S. PATENT DOCUMENTS

| | | | |
|---|---|---|---|
| 2006/0161145 A1* | 7/2006 | Lin | A61B 18/20 606/4 |
| 2007/0025401 A1 | 2/2007 | Hayashi et al. | |
| 2008/0151366 A1* | 6/2008 | Araya | G02B 21/0036 359/385 |
| 2009/0149841 A1 | 6/2009 | Kurtz | |

(Continued)

FOREIGN PATENT DOCUMENTS

| | | |
|---|---|---|
| JP | H11-68218 A | 3/1999 |
| JP | 2005-185408 A | 7/2005 |

(Continued)

OTHER PUBLICATIONS

PolyTech, Deflectors "https://www.polytec.com/eu/optical-systems/products/laser-accessories/electro-optic-components/deflectors".*

(Continued)

*Primary Examiner* — Lynsey C Eiseman
(74) *Attorney, Agent, or Firm* — Oliff PLC

(57) ABSTRACT

A laser treatment apparatus that is configured to irradiate a laser beam to an affected area to treat the affected area. The laser treatment apparatus includes: a beam source device that is configured to output a laser beam; and a scanning device that is configured to scan a therapeutic range including the affected area with the laser beam by irradiating the laser beam to the therapeutic range. The scanning device has a transmission medium that is configured to change an output direction of a laser beam according to an applied voltage.

15 Claims, 9 Drawing Sheets

(56) References Cited

U.S. PATENT DOCUMENTS

| | | | |
|---|---|---|---|
| 2011/0172649 A1* | 7/2011 | Schuele | A61F 9/008 606/4 |
| 2013/0261612 A1 | 10/2013 | Yokosuka et al. | |
| 2015/0182380 A1* | 7/2015 | Miyagi | A61F 9/00825 606/4 |
| 2016/0249982 A1 | 9/2016 | Varghese et al. | |

FOREIGN PATENT DOCUMENTS

| | | |
|---|---|---|
| JP | 2007-29627 A | 2/2007 |
| JP | 2010-538704 A | 12/2010 |
| JP | 2012-213634 A | 11/2012 |
| JP | 2016-193030 A | 11/2016 |
| JP | 2016-539665 A | 12/2016 |

OTHER PUBLICATIONS

Jun. 30, 2020 International Preliminary Report on Patentability issued in International Patent Application No. PCT/JP2018/047268.
Mar. 12, 2019 Search Report issued in International Patent Application No. PCT/JP2018/047268.

* cited by examiner

LASER TREATMENT APPARATUS

CROSS REFERENCE TO RELATED APPLICATION

This application is a continuation-in-part application of International Application No. PCT/JP2018/047268, filed Dec. 21, 2018, which claims priority to Japanese Patent Application No. 2017-249924, filed Dec. 26, 2017. The contents of these applications are incorporated herein by reference in their entirety.

TECHNICAL FIELD

The present disclosure relates to a laser treatment apparatus, and particularly, to a laser treatment apparatus that scans a therapeutic range with a laser beam at a high speed so that an affected area within the therapeutic range can be treated efficiently.

BACKGROUND

Conventionally, some treatment apparatuses, such as a laser treatment apparatus that irradiates a laser beam to an affected area to destroy pigments or the like in the affected area to remove bruises, spots, tattoos, or the like, have been known.

In this type of laser treatment apparatuses, it is necessary to move a target position of a laser beam within a therapeutic range so that the laser beam is irradiated to the entire affected area, and a galvano mirror is used for moving the target position of the laser beam.

Japanese Patent Application Publication No. 2005-185408 discloses a laser treatment apparatus that changes a target position of a laser beam using a galvano mirror.

SUMMARY

As illustrated in FIG. 9, in a laser treatment apparatus 900 disclosed in Japanese Patent Application Publication No. 2005-185408, two galvano mirrors 901 and 902 are used for moving a target position of a laser beam Ls from a beam source in X and Y directions.

However, in the laser treatment apparatus 900 of Japanese Patent Application Publication No. 2005-185408, since a physical driving time of the galvano mirrors 901 and 902 is necessary, it is difficult to move the position of the laser beam Ls at a high speed within a therapeutic range K. Therefore, there is a problem that efficient treatment of an affected area in the therapeutic range K is difficult in the laser treatment apparatus 900.

Moreover, since the laser treatment apparatus does not perform three-dimensional scanning with a very small diameter of a focal point, unnecessary generated heat is applied to normal tissues and results in side effects.

The present disclosure has therefore been made in view of the above problems, and an object thereof is to provide a laser treatment apparatus that scans therapeutic range with a laser beam from a beam source at a high speed to efficiently treat the affected area within the therapeutic range while suppressing side effects on the affected area.

In order to solve the problems, provided is a laser treatment apparatus that is configured to irradiate a laser beam to an affected area to treat the affected area. The laser treatment apparatus includes: a beam source device that is configured to output a laser beam; a polarization varying device that is configured to control polarization of the laser beam output by the beam source device; and a scanning device that is configured to scan a therapeutic range including the affected area with the laser beam of which the polarization is controlled by the polarization varying device by irradiating the laser beam to the therapeutic range. The scanning device has a transmission medium that is configured to change an output direction of the laser beam according to an applied voltage.

Also provided is a laser treatment apparatus that is configured to irradiate a laser beam to an affected area to treat the affected area. The laser treatment apparatus includes: a beam source device that is configured to output a laser beam; a scanning device that is configured to scan a therapeutic range including the affected area with the laser beam by irradiating the laser beam to the therapeutic range; and a focal length adjustment mechanism that is configured to align a focal length of the laser beam output from the scanning device to a depth position of the affected area. The scanning device includes an optical element in which an output direction of the laser beam is changed according to an applied voltage.

DETAILED DESCRIPTION

First Embodiment

[Treatment Apparatus]

Hereinafter, a laser treatment apparatus 1 according to a first embodiment of the present disclosure will be described.

Figure 1:
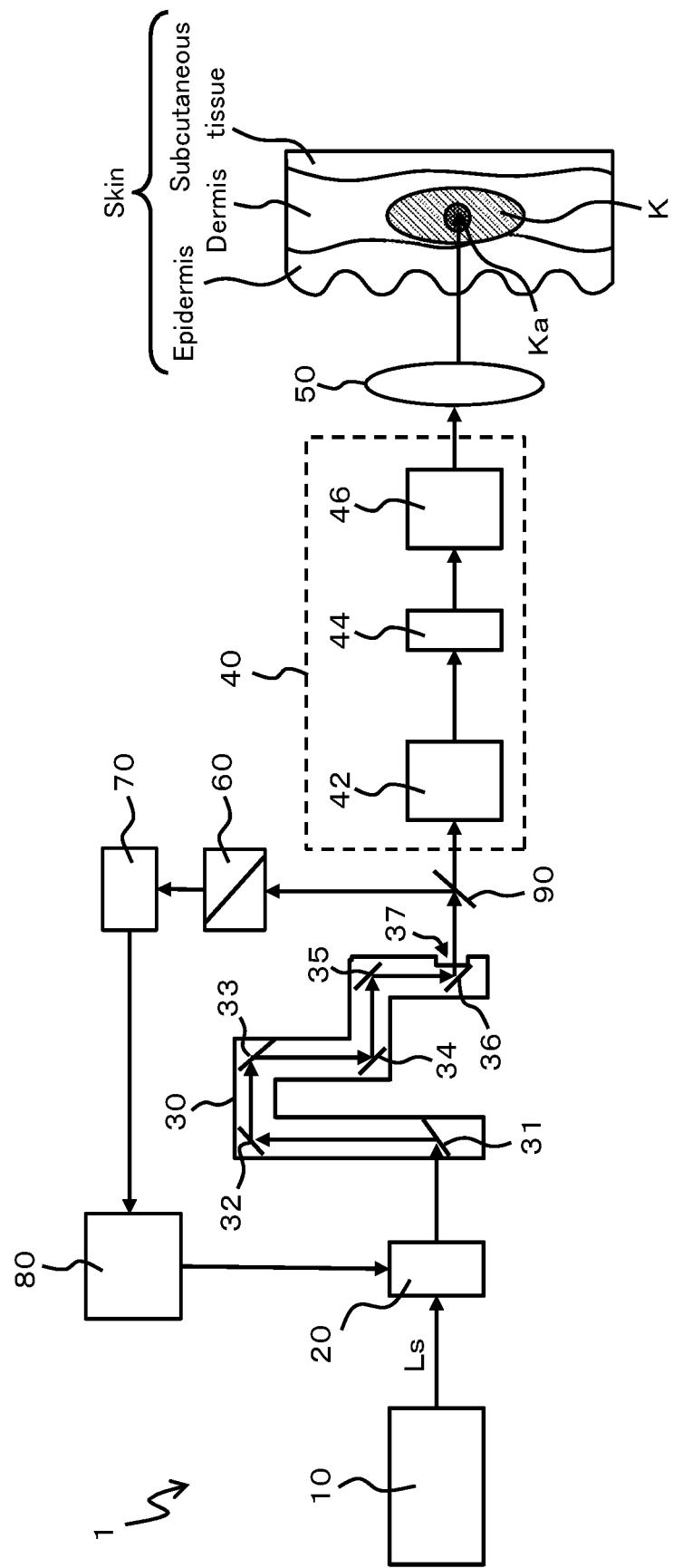
FIG. 1 is a block diagram illustrating the functions of a laser treatment apparatus according to a first embodiment.

FIG. 1 is a block diagram illustrating the functions of the laser treatment apparatus 1 according to a first embodiment.

Figure 2:
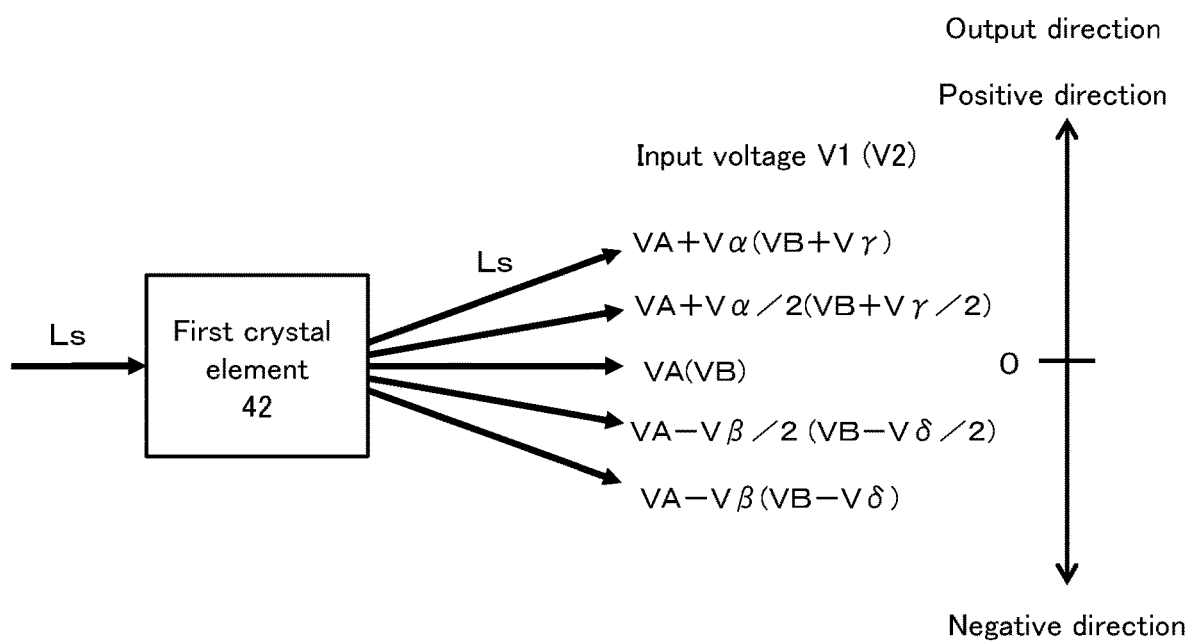
FIG. 2 is a diagram illustrating a first crystal element according to the first embodiment.

FIG. 2 is a diagram illustrating a first crystal element 42 according to the first embodiment.

[Laser Treatment Apparatus]

The laser treatment apparatus 1 includes a beam source 10, a polarization varying device 20, a light guiding device 30, a scanning device 40, and a lens 50. In the laser treatment apparatus 1, a laser beam propagates in a free space when the laser beam travels from the beam source 10 to the lens 50.

Specifically, a laser beam Ls output from the beam source 10 passes through the light guiding device 30 formed of a large number of reflecting plates and is guided up to the lens 50.

The beam source 10 is a device that outputs a laser beam Ls of a predetermined wavelength, and is a fiber laser or the like is used, for example. The beam source 10 outputs a laser beam Ls having a repetition frequency of 1 kHz to 10 MHz with a pulse width of 1 to 1000 picoseconds. The pulse width of the laser beam Ls output by the beam source 10 is more preferably 500 picoseconds or smaller and the repetition frequency is more preferably between 250 kHz and 10 MHz in order to obtain an appropriate treatment effect while preventing the influence of heat on an affected area. A diameter of the laser beam Ls output from the beam source 10 is approximately 1 mm.

The laser beam Ls output from the beam source 10 is incident on the polarization varying device 20.

The polarization varying device 20 has a crystal (not illustrated) that changes a polarization direction of the laser beam Ls having a predetermined vibration direction (a polarization direction) and a movable device (not illustrated) that changes an angle of the crystal (not illustrated). The movable device (not illustrated) is configured as a motor (not illustrated) or the like.

The polarization varying device 20 can change the polarization direction of the laser beam Ls incident from the beam source 10 to a desired polarization direction by changing the angle of the crystal (not illustrated) using the movable device (not illustrated). The polarization varying device 20 can change the polarization direction of the laser beam Ls passing therethrough according to a command of a controller 80 to be described later.

Although the above polarization varying device 20 has a configuration of changing the angle of a crystal using the movable device configured as a motor or the like, the configuration of changing the polarization direction of the laser beam is not limited thereto. For example, the polarization varying device 20 may have a configuration of changing the polarization direction of the laser beam after passing through the crystal by applying an electric field to the crystal. Also, a transmission medium different from the crystal may be used instead of the crystal.

The laser beam Ls having passed through the polarization varying device 20 is incident on the light guiding device 30 with the diameter being increased to approximately 10 to 20 mm using a concave lens or a convex lens (not illustrated).

The light guiding device 30 is a device that guides the laser beam Ls output from the beam source 10 to the vicinity of a therapeutic range K of a patient. In this embodiment, a manipulator-type light guiding device having a plurality of movable joints is used as the light guiding device 30.

A first reflecting plate 31, a second reflecting plate 32, a third reflecting plate 33, a fourth reflecting plate 34, a fifth reflecting plate 35, and a sixth reflecting plate 36 are provided inside the light guiding device 30. In the light guiding device 30, the laser beam Ls incident from the polarization varying device 20 is reflected from the first to sixth reflecting plates 31 to 36 and is guided up to an emission portion 37.

Although, the above light guiding device 30 is a manipulator-type light guiding device having a plurality of movable joints, the light guiding device is not limited thereto as long as it can guide the laser beam Ls to the therapeutic range K, and for example, an optical fiber which is flexible and can maintain polarization may be used. In this case, the polarization state of the laser beam Ls output from the fiber can be maintained in the polarization state of the laser beam Ls before the incidence on the fiber.

The laser beam Ls guided to the emission portion 37 of the light guiding device 30 is incident on a reflecting plate 90.

The reflecting plate 90 reflects a partial laser beam Ls within the incident laser beam Ls toward a polarizer 60 and transmits the other laser beam Ls toward the scanning device 40.

The laser beam Ls having passed through the reflecting plate 90 is incident on the scanning device 40 with the diameter being decreased to approximately 1 mm using a concave lens or a convex lens (not illustrated).

The scanning device 40 has a first crystal element 42, a wavelength plate 44, and a second crystal element 46.

The first crystal element 42 has such a crystal structure that transmits a laser beam Ls having a polarization component in a first direction (for example, a horizontal direction illustrated in FIG. 3) while changing the output direction thereof and transmits a laser beam Ls having the other polarization component without changing the output direction thereof. The first crystal element 42 is a crystal element having an electro-optical effect, and a predetermined input voltage V1 is applied to the first crystal element 42.

A crystal structure inside the first crystal element 42 changes according to the magnitude (magnetic field) of the applied input voltage V1 whereby a refractive index thereof changes and a target position in a horizontal direction of the laser beam Ls is changed. LN (lithium tantalate), LT (lithium niobate), or KTN crystals having an electro-optical effect, for example, can be used as the first crystal element 42.

As illustrated in FIG. 2, an input voltage V1 of $VA-V\beta$ to $VA+V\alpha$, for example, is applied to the first crystal element 42.

When the input voltage V1 of the first crystal element 42 is a predetermined reference voltage VA, an output direction of the laser beam Ls is the same vector as the incidence direction. When the input voltage V1 of the first crystal element 42 is increased by $V\alpha$ in a plus direction from the reference voltage VA, the laser beam Ls is displaced in a plus direction (the rightward direction in FIG. 3) of the horizontal direction. When the input voltage V1 of the first crystal element 42 is increased VP in a minus direction from the reference voltage VA, the laser beam Ls is displaced in a minus direction (the leftward direction in FIG. 3) of the horizontal direction.

In this way, the refractive index of the first crystal element 42 is changed according to the input voltage V1 whereby the emission position of the laser beam Ls can be adjusted to a predetermined position on the same straight line (the same horizontal direction).

Returning to FIG. 1, in the scanning device 40, the laser beam Ls output from the first crystal element 42 is incident on the wavelength plate 44.

The wavelength plate 44 gives a predetermined phase difference to the incident laser beam Ls and outputs the laser beam Ls. In this embodiment, a $\lambda/2$ wavelength plate that gives a phase difference of $\pi$ (180 degrees) to the incident laser beam Ls and outputs the laser beam Ls is used as the wavelength plate 44. In this way, the polarization direction of the laser beam Ls is rotated by 90 degrees.

In the scanning device 40, the laser beam Ls output from the wavelength plate 44 is incident on the second crystal element 46.

The second crystal element 46 is also a crystal element having an electro-optical effect, and is a crystal of LN, LT, or KTN having the same structure and function as those of the first crystal element 42 described above. The second crystal element 46 has such a property that transmits a laser beam Ls having a polarization component in a second direction (for example, a vertical direction illustrated in FIG. 3) orthogonal to the first direction (for example, the horizontal direction illustrated in FIG. 3) while changing the output direction thereof and transmits a laser beam Ls having the other polarization component without changing the output direction thereof.

In this embodiment, an input voltage V2 of VB−Vδ to VB+Vγ is also applied to the second crystal element 46.

When the input voltage V2 of the second crystal element 46 is a predetermined reference voltage VB, the output direction of the laser beam Ls is the same vector as the input direction. When the input voltage V2 of the second crystal element 46 is increased by Vγ in a plus direction from the reference voltage VB, the laser beam Ls is displaced in a plus direction (the downward direction in FIG. 3) of the second direction (the vertical direction in FIG. 3) orthogonal to the first direction (the horizontal direction in FIG. 3). When the input voltage V2 of the second crystal element 46 is increased by Vδ in a minus direction from the reference voltage VA, the laser beam Ls is displaced in a minus direction (the upward direction in FIG. 3) of the vertical direction.

In this way, the refractive index of the second crystal element 46 is changed according to the input voltage V2 whereby the output position of the laser beam Ls can be adjusted to a predetermined position on the same straight line (the vertical direction).

In the laser treatment apparatus 1, the laser beam Ls can be moved to an arbitrary position in the horizontal direction and the vertical direction (see FIG. 3) of the therapeutic range K with the aid of the first and second crystal elements 42 and 46.

A configuration including the first and second crystal elements 42 and 46 corresponds to a crystal element. Moreover, a configuration including the first and second crystal element 42 and 46 corresponds to a transmission medium (a first transmission medium and a second transmission medium) that changes an output direction of a laser beam according to an applied voltage.

As illustrated in FIG. 1, the laser beam Ls having passed through the scanning device 40 (the second crystal element 46) is irradiated to a predetermined therapeutic range K of the skin via the lens 50 to destroy pigments or tissues in an affected area Ka of the therapeutic range K. In this way, removal (treatment) of pigments or tissues can be performed by the laser treatment apparatus 1.

The diameter of the laser beam Ls irradiated to the therapeutic range K is decreased by the lens 50 and is adjusted to a range of approximately 20 μm to 100 μm.

[Laser Beam Moving Method]

Here, a method for moving the laser beam Ls in the therapeutic range K will be described.

Figure 3:
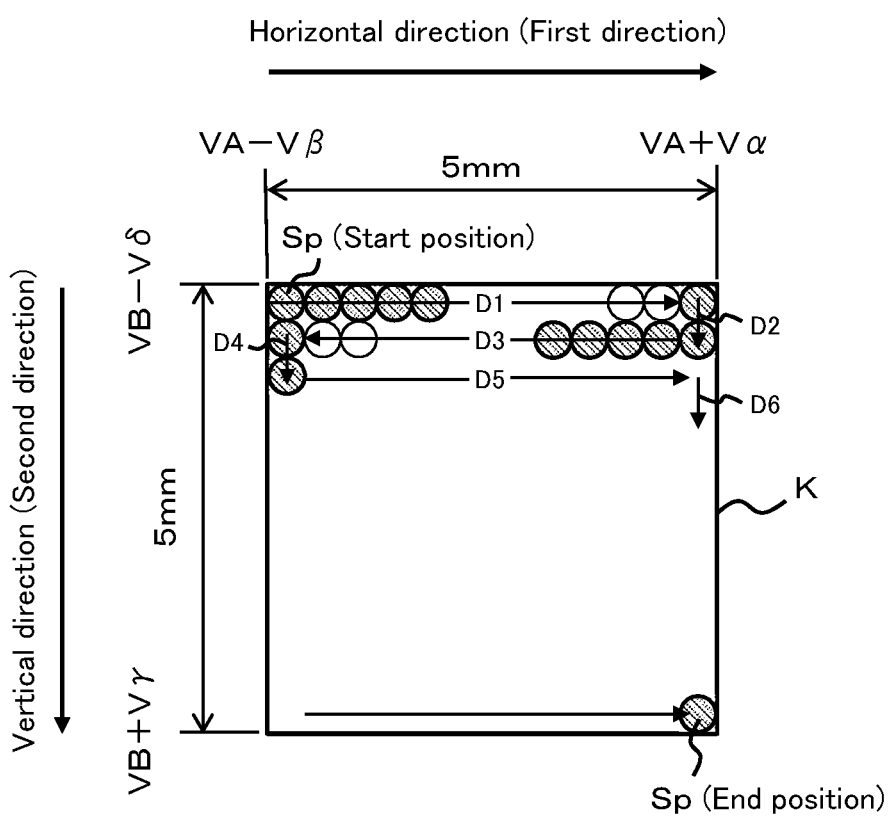
FIG. 3 is a diagram illustrating an example of a method for moving a focal point (a spot) of a laser beam irradiated to a therapeutic range.

FIG. 3 is a diagram illustrating an example of a method for moving the focal point (the spot) Sp of the laser beam Ls irradiated to the therapeutic range K and is a front view of the therapeutic range K.

In FIG. 3, a left-right direction will be defined as a horizontal direction or a first direction, and an up-down direction will be defined as a vertical direction or a second direction. In this embodiment, a case in which a range of 5 mm×5 mm is set as the therapeutic range K will be described.

As described above, the position in the horizontal direction (the first direction) of the spot Sp of the laser beam Ls irradiated to the therapeutic range K changes according to the input voltage V1 (the electric field) applied to the first crystal element 42. In this embodiment, the position in the horizontal direction of the spot Sp of the laser beam Ls is set such that the position is at the leftmost position in the therapeutic range K when VA−Vβ is applied to the first crystal element 42, the position is at the rightmost position in the therapeutic range K when VA+Vα is applied to the first crystal element 42, and the position is at the center position of the therapeutic range K when the reference voltage VA is applied to the first crystal element 42.

The position in the vertical direction (the second direction) of the spot Sp of the laser beam Ls irradiated to the therapeutic range K changes according to the input voltage V2 (the electric field) applied to the second crystal element 46. In this embodiment, the position in the vertical direction of the spot Sp of the laser beam Ls is set such that the position is at the uppermost position in the therapeutic range K when VB−Vγ is applied to the second crystal element 46, the position is at the lowermost position in the therapeutic range K when VB+Vδ is applied to the second crystal element 46, and the position is at the center position of the therapeutic range K when the reference voltage VB is applied to the second crystal element 46.

In the laser treatment apparatus 1, the input voltages V1 and V2 (the electric field) applied to the first and second crystal elements 42 and 46 are controlled and irradiation of the laser beam Ls starts from a start point (the start position of the spot Sp in FIG. 3) of the leftmost position or the uppermost position of the therapeutic range K.

In the laser treatment apparatus 1, the input voltages V1 and V2 (the electric field) applied to the first and second crystal elements 42 and 46 are controlled, the position of the spot Sp of the laser beam Ls is sequentially moved rightward by the spot diameter from the leftmost position in the horizontal direction of the therapeutic range K to the rightmost position, and the laser beam Ls is irradiated whenever the position of the spot Sp is sequentially moved rightward (see a moving direction D1 in FIG. 3).

In the laser treatment apparatus 1, after irradiation of the laser beam Ls at the rightmost position in the horizontal direction of the therapeutic range K ends, the position of the spot Sp of the laser beam Ls is moved in a downward direction of the vertical direction by the spot diameter of the laser beam Ls (see a moving direction D2 in FIG. 3) to radiate the laser beam Ls.

In the laser treatment apparatus 1, the input voltages V1 and V2 (the electric field) applied to the first and second crystal elements 42 and 46 are controlled, the position of the spot Sp of the laser beam Ls is sequentially moved (see a moving direction D3 in FIG. 3) in a leftward direction by the spot diameter from the rightmost position in the horizontal direction of the therapeutic range K to the leftmost position, and the laser beam Ls is irradiated whenever the position of the spot Sp is moved sequentially leftward.

In the laser treatment apparatus 1, after irradiation of the laser beam Ls at the leftmost position of the horizontal direction of the therapeutic range K ends, the position of the spot Sp of the laser beam Ls is moved in a downward direction of the vertical direction by the spot diameter of the laser beam Ls (see a moving direction D4 in FIG. 3) by irradiating the laser beam Ls.

In the laser treatment apparatus 1, the movement of the position of the spot Sp of the laser beam Ls and the irradiation of the laser beam Ls are repeated until the spot Sp reaches the end position (see FIG. 3) of the spot Sp, which is the rightmost position or the lowermost position (see moving directions D5 and D6 in FIG. 3).

In the laser treatment apparatus 1, by scanning with the laser beam Ls in this manner, it is possible to irradiate the laser beam Ls uniformly to the entire therapeutic range K.

A method for moving the laser beam Ls in the laser treatment apparatus 1 is not limited to the above method. For example, scanning with the laser beam Ls may be performed by a method similar to the above method from a top-right corner to a bottom-left corner. Moreover, scanning with the laser beam may be performed in a spiral form so as to draw a circle from the center of the therapeutic range K toward the outer side and may be performed along the trajectory of a Lissajous curve. Furthermore, in the laser treatment apparatus 1, the laser beam used in the respective scanning methods may be irradiated with a gap between adjacent irradiated beams and may be irradiated in an overlapping manner so that the gap between adjacent irradiated beams is filled.

Figure 4:
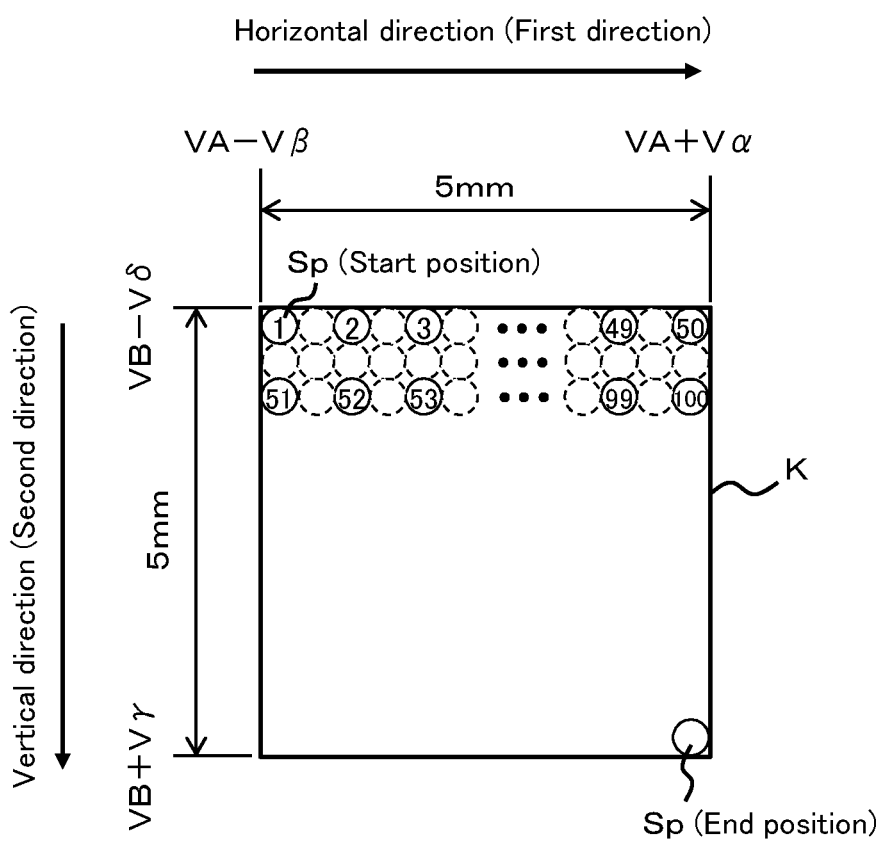
FIG. 4 is a diagram illustrating another example of a method for moving a focal point (a spot) of a laser beam irradiated to a therapeutic range.

FIG. 4 is a diagram illustrating another example of a method for moving the focal point (the spot) Sp of a laser beam Ls irradiated to the therapeutic range K and is a front view of the therapeutic range K.

In FIG. 4, a left-right direction will be defined as a horizontal direction or a first direction, and an up-down direction will be defined as a vertical direction or a second direction.

As illustrated in FIG. 4, in the laser treatment apparatus 1, the input voltages V1 and V2 (the electric field) applied to the first and second crystal elements 42 and 46 are controlled, and irradiation of the laser beam Ls starts from a start point (a starting position of the spot Sp in the drawing) which is at the leftmost position or the uppermost position of the therapeutic range K.

In the laser treatment apparatus 1, the input voltages V1 and V2 (the electric field) applied to the first and second crystal elements 42 and 46 are controlled, the position of the spot Sp of the laser beam Ls is sequentially moved rightward with an interval corresponding to one spot diameter from the leftmost position in the horizontal direction of the therapeutic range K to the rightmost position (see positions 1 to 50 of the spot Sp), and the laser beam Ls is irradiated whenever the position of the spot Sp is sequentially moved rightward. The laser beam Ls may be moved with an interval corresponding to two spot diameters or more and may be moved with an interval corresponding to one spot diameter.

Subsequently, in the laser treatment apparatus 1, the position of the spot Sp of the laser beam Ls is moved to the leftmost position in the downward direction with an interval corresponding to one spot diameter and is sequentially moved rightward with an interval corresponding to one spot diameter from the leftmost position in the horizontal direction of the therapeutic range K to the rightmost position (see positions 51 to 100 of the spot Sp), and the laser beam Ls is irradiated whenever the position of the spot Sp is sequentially moved rightward. The laser beam Ls may be moved with an interval corresponding to two spot diameters or more and may be moved with an interval equivalent to or smaller than one spot diameter.

In the laser treatment apparatus 1, the movement of the position of the spot Sp of the laser beam Ls and the irradiation of the laser beam Ls are repeated until the spot Sp reaches the end position (see FIG. 4) of the spot Sp.

In this manner, in the laser treatment apparatus 1, the laser beam Ls is irradiated with an interval in the horizontal direction and the vertical direction. Therefore, in the laser treatment apparatus 1, since the laser beam Ls is continuously irradiated at intervals, heat of the laser beam Ls is not accumulated in a superimposed manner, and occurrence of local heating can be prevented. As a result, it is possible to suppress damage to normal tissues due to heat of the therapeutic range K and to decrease the time (down-time) to recovery after a medical procedure ends.

Particularly, since the laser treatment apparatus 1 uses the laser beam Ls having a high repetition frequency of 1 kHz to 10 MHz (preferably 250 kHz to 10 MHz) with a very short pulse with of 1 to 1000 picoseconds (preferably 500 picoseconds or smaller), it is possible to shorten the scanning time with the laser beam Ls. For example, in this type of laser treatment apparatus 1, it is necessary to move the laser beam Ls irradiated to one therapeutic range K to the next therapeutic range K in a very short irradiation time of 0.3 seconds or smaller. In such a case, since the repetition frequency of the laser beam Ls is high, scanning of a predetermined entire therapeutic range K can be performed appropriately in a short time.

In the laser treatment apparatus 1, since the spot diameter of the laser beam Ls irradiated to the therapeutic range K is as small as 20 to 100 μm, irradiation of the laser beam Ls optimal to the state of the affected area Ka can be performed with a fine irradiation pattern for the therapeutic range K. Since irradiation of the laser beam Ls optimal to the state of the affected area Ka can be performed, it is possible to prevent the influence of heat due to heating of a predetermined region.

Although the laser beam Ls is irradiated at intervals as described above, in order to move the laser beam Ls at a high speed, irradiation of the laser beam Ls may start to a position displaced by one spot diameter from the end position of the spot Sp after the laser beam Ls reaches the end position so as to fill the interval.

Returning to FIG. 1, in this embodiment, the reflecting plate 90 is provided between the light guiding device 30 and the scanning device 40, and the laser beam Ls output from the light guiding device 30 is incident on the reflecting plate 90.

The laser beam Ls incident on the reflecting plate 90 is divided into a laser beam Ls which passes through the reflecting plate 90 and is incident on the scanning device 40 and a laser beam Ls which is reflected from the reflecting plate 90 and is incident on the polarizer 60.

The polarizer 60 has a structure of transmitting the laser beam Ls having a predetermined polarization component. In this embodiment, the polarizer 60 is disposed so as to transmit a laser beam Ls having the same polarization component as when passing through the first crystal element 42. That is, the polarizer 60 transmits the laser beam Ls having the polarization component and blocks the other polarization component. In this way, the laser beam Ls having the same polarization component as the laser beam Ls having passed through the first crystal element 42 is incident on a detector 70.

The detector 70 is a device that detects the intensity of the laser beam Ls and detects the intensity of the laser beam Ls incident from the polarizer 60. The detection result in the detector 70 is transmitted to the controller 80.

The controller 80 controls the polarization varying device 20 so that the intensity of the laser beam Ls detected by the detector 70 is maximized. Specifically, the controller 80 controls the polarization varying device 20 to adjust the polarization direction of the laser beam Ls output from the polarization varying device 20 so as to coincide with the polarization direction of the polarizer 60. Therefore, the intensity of the laser beam Ls detected by the detector 70, having passed through the polarizer 60 is maximized.

In this way, the laser treatment apparatus 1 can control the intensity of the laser beam Ls output from the scanning device 40 (the first and second crystal elements 42 and 46) so as to be maximized and perform treatment of the affected area Ka efficiently using the laser beam Ls. Moreover, since the scanning device 40 move widely with respect to a treatment target area, stable treatment can be performed by adjusting the polarization state as necessary. The polarizer 60 may be disposed so as to transmit a laser beam Ls having a polarization component orthogonal to that of the laser beam Ls passing through the first crystal element 42. In this case, the controller 80 controls the polarization varying device 20 so that the intensity of the laser beam Ls detected by the detector 70 is minimized. Moreover, although an example in which the detector 70 is disposed on a transmission side of the polarizer 60 has been illustrated, the detector 70 may be disposed on a reflection side.

As described above, the first embodiment is configured as follows:

(1) The laser treatment apparatus 1 that irradiates the laser beam Ls to the affected area Ka to treat the affected area Ka includes the beam source 10 (a beam source device) that outputs the laser beam Ls and the scanning device 40 that scans the therapeutic range K including the affected area Ka with the laser beam Ls by irradiating the laser beam Ls to the therapeutic range K, in which the scanning device 40 has a crystal element in which an output direction of the laser beam Ls changes according to an applied input voltage V (electric field).

With this configuration, since the scanning device 40 can changes the output direction of the laser beam Ls according to the input voltage V (the electric field), a physical driving time for changing the output direction of the laser beam Ls is not necessary. Therefore, the laser treatment apparatus 1 can scan the therapeutic range K with the laser beam Ls output from the beam source 10 at a high speed with the aid of the scanning device 40 and perform treatment of the affected area Ka efficiently using the laser beam Ls. In this embodiment, although the scanning device 40 is configured using a crystal element, another transmission medium that changes the output direction of the laser beam according to an applied voltage may be used.

(2) The crystal element includes the first crystal element 42 that changes the output direction of the laser beam Ls polarized in a first direction (a horizontal direction) by the polarization varying device 20 according to the applied input voltage V1 and the second crystal element 46 that changes the output direction of the laser beam Ls polarized in a second direction (a vertical direction) orthogonal to the first direction (the horizontal direction) according to the applied input voltage V2.

With this configuration, the laser treatment apparatus 1 can scan the therapeutic range K freely in both the horizontal direction and the vertical direction with the laser beam Ls when seen in a plan view with the aid of the first and second crystal elements 42 and 46. Therefore, the laser treatment apparatus 1 can perform scanning and irradiation of the laser beam Ls uniformly in the entire therapeutic range K with a simple configuration using the first and second crystal elements 42 and 46.

(3) The laser treatment apparatus further includes the controller 80 that controls the polarization varying device 20 and the detector 70 (an optical detection device) that detects the intensity of the laser beam Ls output by the beam source 10, and the controller 80 controls the polarization direction of the laser beam Ls polarized by the polarization varying device 20 on the basis of the detection result (the intensity of light) of the laser beam Ls obtained by the detector 70.

With this configuration, in the laser treatment apparatus 1, the polarization state of the laser beam Ls incident to the first and second crystal elements 42 and 46 can be controlled to be in an optimal polarization direction determined by the crystal structures of the respective crystal elements 42 and 46. Therefore, the laser treatment apparatus 1 can maximize the output of the laser beam Ls output from the first and second crystal elements 42 and 46 and perform treatment of the affected area Ka efficiently.

Particularly, when the laser treatment apparatus 1 has the manipulator-type light guiding device 30 having a plurality of movable joints, the polarization direction of the laser beam Ls may change due to movement of the light guiding device 30 or the like, and the laser beam Ls output from the first crystal element 42 may be output in a split manner. Therefore, the controller 80 controls the polarization varying device 20 on the basis of the detection result in the detector 70 whereby the polarization direction of the laser beam Ls changed due to the movement of the light guiding device 30 can be corrected appropriately. As a result, even if a user moved the light guiding device 30, treatment of the affected area Ka can be performed safely and with high reproducibility.

(4) The laser treatment apparatus further includes the polarizer 60 provided on an incidence side of the laser beam Ls incident to the detector 70, the detector 70 is provided on an upstream side (between the polarization varying device 20 and the first crystal element 42) of the first crystal element 42 in the path of the laser beam Ls, and the controller 80 controls the polarization direction of the laser beam Ls polarized by the polarization varying device 20 on the basis of the detection result of the laser beam Ls detected by the detector 70 via the polarizer 60.

With this configuration, in the laser treatment apparatus 1, the polarization direction of the laser beam Ls incident on the first crystal element 42 can be controlled to be in an optimal polarization direction determined by the crystal structure of the first crystal element 42 on the basis of the polarization direction of the laser beam Ls immediately before being incident on the first crystal element 42. Therefore, the laser treatment apparatus 1 can optimize the intensity of the laser beam Ls output from the first crystal element 42 quickly and perform treatment of the affected area Ka efficiently.

(5) The beam source 10 outputs a laser beam having a repetition frequency of 1 kHz to 10 MHz with a pulse width of 1 to 1000 picoseconds.

With this configuration, since the repetition frequency of the laser beam Ls output from the beam source 10 is as high as 1 kHz to 10 MHz, the laser treatment apparatus 1 can accelerate scanning of the entire therapeutic range K with the laser beam Ls and suppress an artificial error such as hand-shake. Moreover, in the laser treatment apparatus 1, since the pulse width of the laser beam Ls is as short as 1 to 1000 picoseconds, it is possible to reduce the influence of heat on the affected area Ka to alleviate the pain during treatment and reduce the down-time.

(6) Particularly, the beam source 10 outputs a laser beam having a repetition frequency of 250 kHz to 10 MHz with a pulse width of 500 picoseconds or smaller.

With this configuration, since the repetition frequency of the laser beam Ls output from the beam source 10 can be set in a very high range, it is possible to radiate the laser beam to more spots and to reduce the influence of heat on the affected area Ka to alleviate the pain during treatment and reduce the down-time. Furthermore, irradiation errors resulting from hand-shake during laser irradiation may not occur easily.

(7) The first and second crystal elements 42 and 46 are at least one of LN crystals, LT crystals, or KTN crystals.

With this configuration, the crystal structure of the crystals such as LN, LT, or KTN change according to an applied input voltage V (electric field). The refractive index of the crystals such as LN, LT, or KTN changes with change in the crystal structure, and the output direction of the laser beam Ls can be adjusted. Therefore, the laser treatment apparatus 1 can freely adjust the output direction of the crystal element by controlling the input voltage V (electric field) applied to the crystal element and perform scanning of an entire predetermined therapeutic range K at a high speed and accurately.

Although the laser beam Ls transmitted from the polarization varying device 20 propagates up to the scanning device 40 with a beam diameter of 10 to 20 mm through the light guiding device 30 in the above laser treatment apparatus 1, the laser beam Ls may propagate with a beam diameter of approximately 1 mm using an optical axis adjustment mechanism 300 that stabilizes the position of the laser beam Ls after the emission portion 37. In this case, the laser beam Ls output from the polarization varying device 20 is caused to propagate while maintaining a beam diameter of approximately 1 mm with the aid of a lens (not illustrated) so as to be incident on the light guiding device 30.

Here, the optical axis adjustment mechanism 300 of a laser treatment apparatus 1A according to a variation example will be described.

Figure 5:
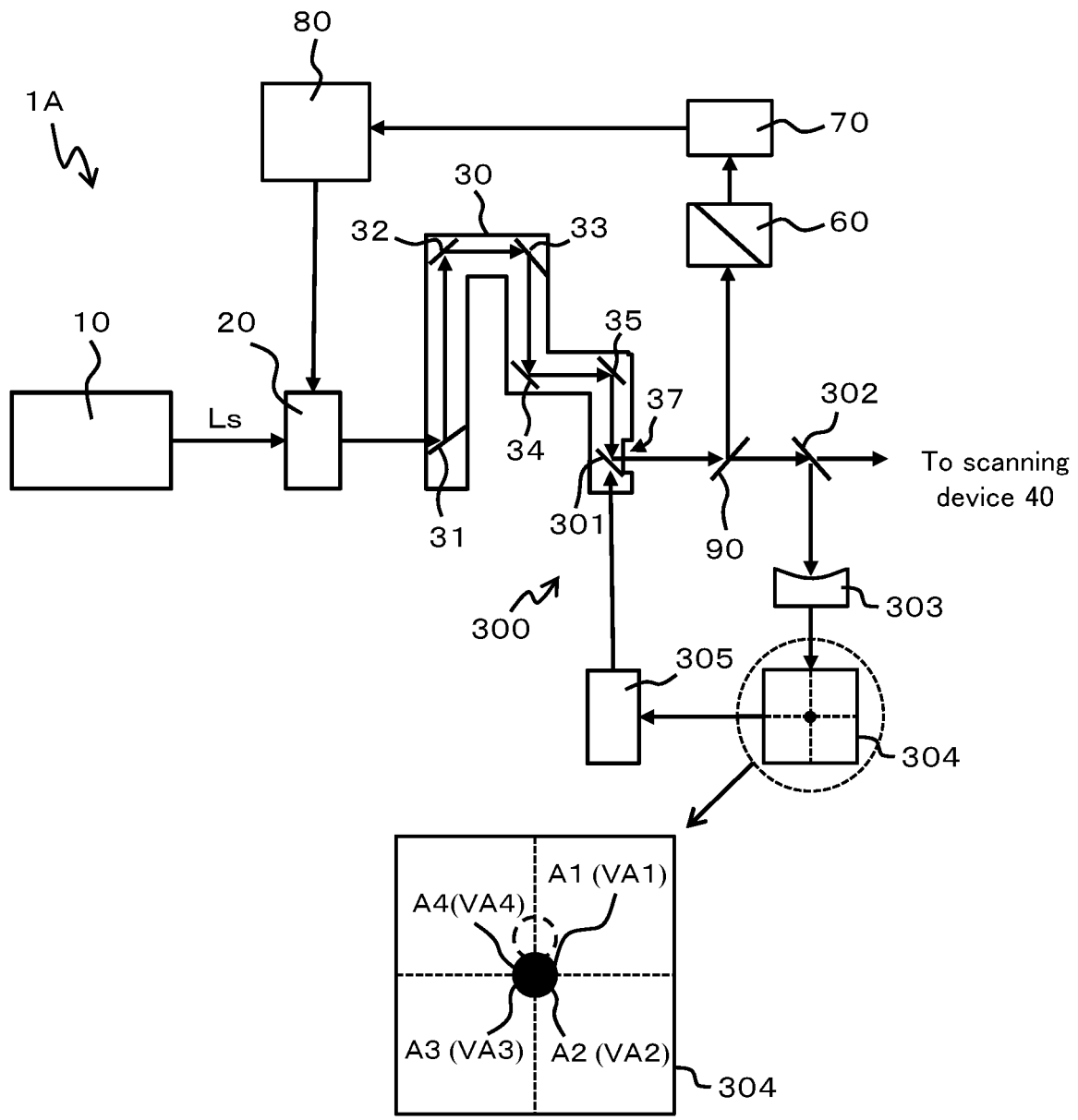
FIG. 5 is a block diagram illustrating an optical axis adjustment mechanism of a laser treatment apparatus according to a variation example.

FIG. 5 is a block diagram illustrating the optical axis adjustment mechanism 300 of the laser treatment apparatus 1A according to the variation example.

As illustrated in FIG. 5, the optical axis adjustment mechanism 300 includes a piezoelectric mirror 301, a reflecting plate 302, a concave lens 303, a quadrant detector 304, and a controller 305.

The piezoelectric mirror 301 has such a property that an inclination thereof changes according to an applied voltage and is controlled by the controller 305.

A portion of the laser beam Ls output from the light guiding device 30 is incident to the concave lens 303 with the aid of the reflecting plate 302, and the laser beam Ls output from the concave lens 303 is incident to the quadrant detector 304.

The quadrant detector 304 has a light-receiving section which is divided into four sections and can detect the light intensities of the four divided light-receiving sections A1 to A4.

The controller 305 detects the voltage values of the respective light-receiving sections A1 to A4 of the quadrant detector 304 and determines that the laser beam Ls is positioned at the center (a black point in broken lines in FIG. 5) if the voltage values of the respective light-receiving sections A1 to A4 are equal.

On the other hand, when there is a bias in the detected respective voltage values of the light-receiving sections A1 to A4, the controller 305 determines that the laser beam Ls is not positioned at the center and controls the piezoelectric mirror 301 so that the respective voltage values of the light-receiving sections A1 to A4 are equal.

For example, when a voltage value VA1 of the light-receiving section A1 and a voltage value VA4 of the light-receiving section A4 are larger than a voltage value VA2 of the light-receiving section A2 and a voltage value VA3 of the light-receiving section A3 (see a dot line in FIG. 5), the controller 305 determines that the laser beam Ls is positioned above and controls the piezoelectric mirror 301 to adjust an up-down direction so that the voltage values VA1 to VA4 are equal.

Although a case of using the quadrant detector 304 in which the light-receiving section is divided into four sections has been described in this embodiment, the number of divisions is not limited thereto. For example, the light-receiving section may be divided into nine or sixteen sections, and by doing so, the detection accuracy of the laser beam Ls is improved. Moreover, four detectors or other numbers of detectors may be arranged.

(8) In the above variation example, the laser treatment apparatus includes the optical axis adjustment mechanism 300 that adjusts the optical axis of the laser beam Ls, the optical axis adjustment mechanism 300 includes the quadrant detector 304 (an optical detection device) that detects a laser beam, the piezoelectric mirror 301 (an optical axis adjuster) that adjusts the optical axis of the laser beam Ls, and the controller 305 (an adjuster controller) that controls the piezoelectric mirror 301, and the controller 305 controls the piezoelectric mirror 301 according to a light intensity of the laser beam Ls detected by the quadrant detector 304.

With this configuration, even when the beam diameter of the laser beam Ls is approximately 1 mm, it is possible to adjust the optical axis position of the laser beam Ls appropriately.

Second Embodiment

Next, a laser treatment apparatus 1B according to a second embodiment will be described.

The laser treatment apparatus 1B according to the second embodiment is different from that of the above embodiment in that the laser treatment apparatus 1B controls the polarization varying device 20 on the basis of the detection result of the laser beam Ls between the first and second crystal elements 42 and 46.

The same components of the laser treatment apparatus 1B according to the second embodiment as those of the laser treatment apparatus 1 according to the above embodiment will be denoted by the same reference numerals, and the description will be provided as necessary.

Figure 6:
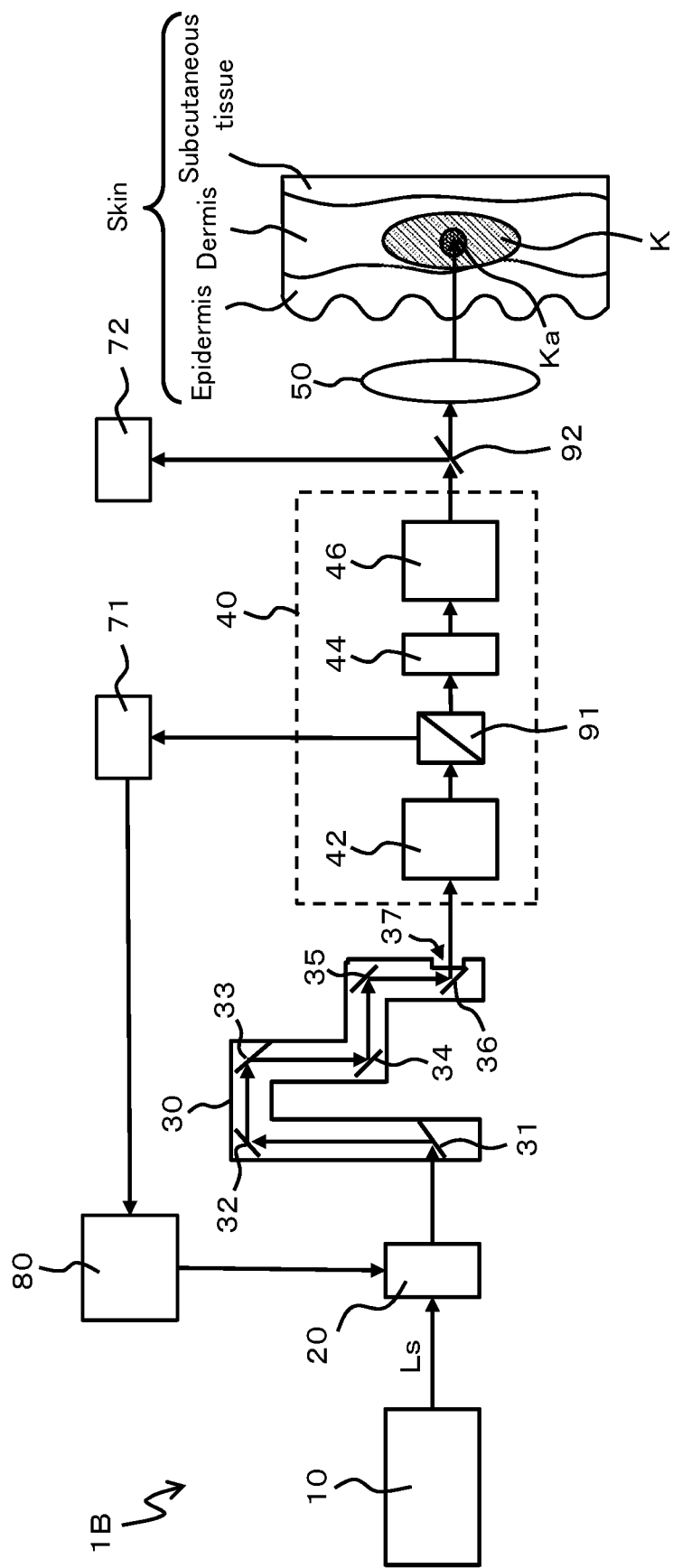
FIG. 6 is a block diagram illustrating the functions of a laser treatment apparatus according to a second embodiment.

FIG. 6 is a block diagram illustrating the function of the laser treatment apparatus 1B according to the second embodiment.

As illustrated in FIG. 6, in the laser treatment apparatus 1B, a polarizer 91 and a detector 71 are provided between the first crystal element 42 and the wavelength plate 44 (the second crystal element 46), and a reflecting plate 92 and a detector 72 are provided on a downstream side of the scanning device 40.

The polarizer 91 reflects a polarization component different from transmissive polarization components (in the embodiment, a horizontal direction) among the polarization components of the laser beam Ls output from the first crystal element 42 toward the detector 71.

The detector 71 detects the intensity of the laser beam Ls output from the first crystal element 42 and transmits the detection result (the intensity of light) to a controller 80.

The controller 80 controls the polarization varying device 20 on the basis of the detection result obtained by the detector 71 so that the intensity of the laser beam Ls detected by the detector 71 is minimized.

In this way, the laser treatment apparatus 1B can adjust the laser beam Ls output from the first crystal element 42 so as to be maximized by controlling the laser beam Ls output from the first crystal element 42 so as to be minimized and can perform treatment of the affected area Ka efficiently. Moreover, since an actual measurement value can be detected by detecting the laser beam Ls between the first and second crystal elements 42 and 46 even when the rotation direction of the scanning device 40 is not fixed with respect to the optical axis, a satisfactory output efficiency is obtained. Moreover, since components of which the output direction is not changed by the first crystal element 42 can be blocked by the polarizer 91 without allowing the components to propagate toward the skin, high safety is guaranteed.

A reflecting plate (not illustrated) and a detector (not illustrated) that detects light from the reflecting plate may be disposed between the first crystal elements 42 and the polarizer 91, and the polarization varying device 20 may be controlled so that the intensity of the laser beam Ls detected by the detector 71 is weakened in a region in which the intensity of the laser beam Ls detected by the detector (not illustrated) is strong.

Alternatively, components of the laser beam Ls of which the output direction is not changed by the first crystal element 42 may be guided to a reflecting plate (not illustrated) and a detector (not illustrated), and the polarization varying device 20 may be controlled so that the intensity of the laser beam Ls detected by the detector 71 is weakened in a region in which the intensity of the laser beam Ls detected by the detector is weak.

Although the polarizer 91 is used for controlling the polarization varying device 20, the reflecting plate 90 and the polarizer 60 may be disposed instead of the polarizer 91 similarly to the first embodiment and the polarization varying device 20 may be controlled so that the intensity of the laser beam Ls detected by the detector 70 is maximized.

Returning to FIG. 6, the reflecting plate 92 and the detector 72 detect the laser beam Ls on a downstream side of the scanning device 40 whereby it is possible to ascertain that the laser beam Ls is output appropriately and to observe the stability of laser output.

The detector 72 may include a plurality of detectors which may be disposed in a range corresponding to the start position and the end position of the spot Sp so as to check whether the scanning range is appropriate.

As described above, the second embodiment is configured as follows:

(9) The detector 71 is provided on a downstream side (between the first and second crystal elements 42 and 46) of the first crystal element 42 on the path of the laser beam Ls, and the controller 80 controls the polarization direction of the laser beam Ls polarized by the polarization varying device 20 on the basis of the detection result of the laser beam Ls detected by the detector 71.

With this configuration, advantages similar to those of the above embodiment are obtained, and since the laser treatment apparatus 1B can detect an actual measurement value by detecting the laser beam Ls between the first and second crystal elements 42 and 46 even when the rotation direction of the scanning device 40 is not fixed with respect to the optical axis, more satisfactory output efficiency is obtained. Moreover, since components of which the output direction is not changed by the first crystal element 42 can be blocked by the polarizer 91 without allowing the components to propagate toward the skin, high safety is guaranteed.

In the laser treatment apparatus 1B, by observing the laser scanning range and the stability of the laser output with the aid of the detector 72, it is possible to further enhance safety.

Third Embodiment

Next, a laser treatment apparatus 1C according to a third embodiment will be described.

The laser treatment apparatus 1C according to the third embodiment is different from that of the above embodiments in that the laser treatment apparatus 1C includes a focal length adjustment mechanism 200 that detects the depth of the affected area Ka and changes the focal length (the position in a depth direction) of the spot Sp of the laser beam Ls according to the detected depth of the affected area Ka.

The same components of the laser treatment apparatus 1C according to the third embodiment as those of the laser treatment apparatus 1 according to the above embodiment will be denoted by the same reference numerals, and the description will be provided as necessary.

Figure 7:
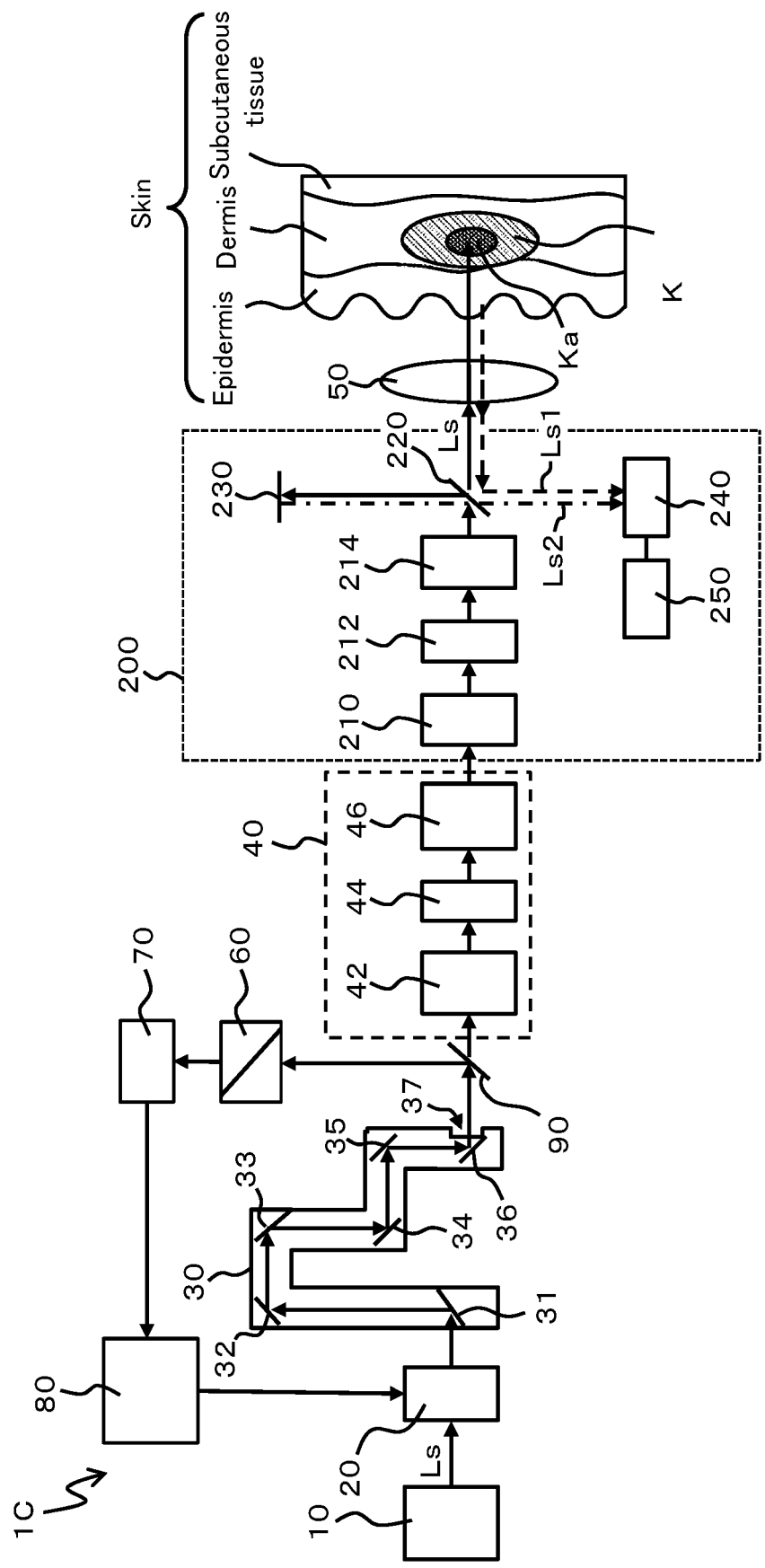
FIG. 7 is a block diagram illustrating main parts of a laser treatment apparatus according to a third embodiment.

FIG. 7 is a block diagram illustrating the function of the laser treatment apparatus 1C according to the third embodiment.

Figure 8:
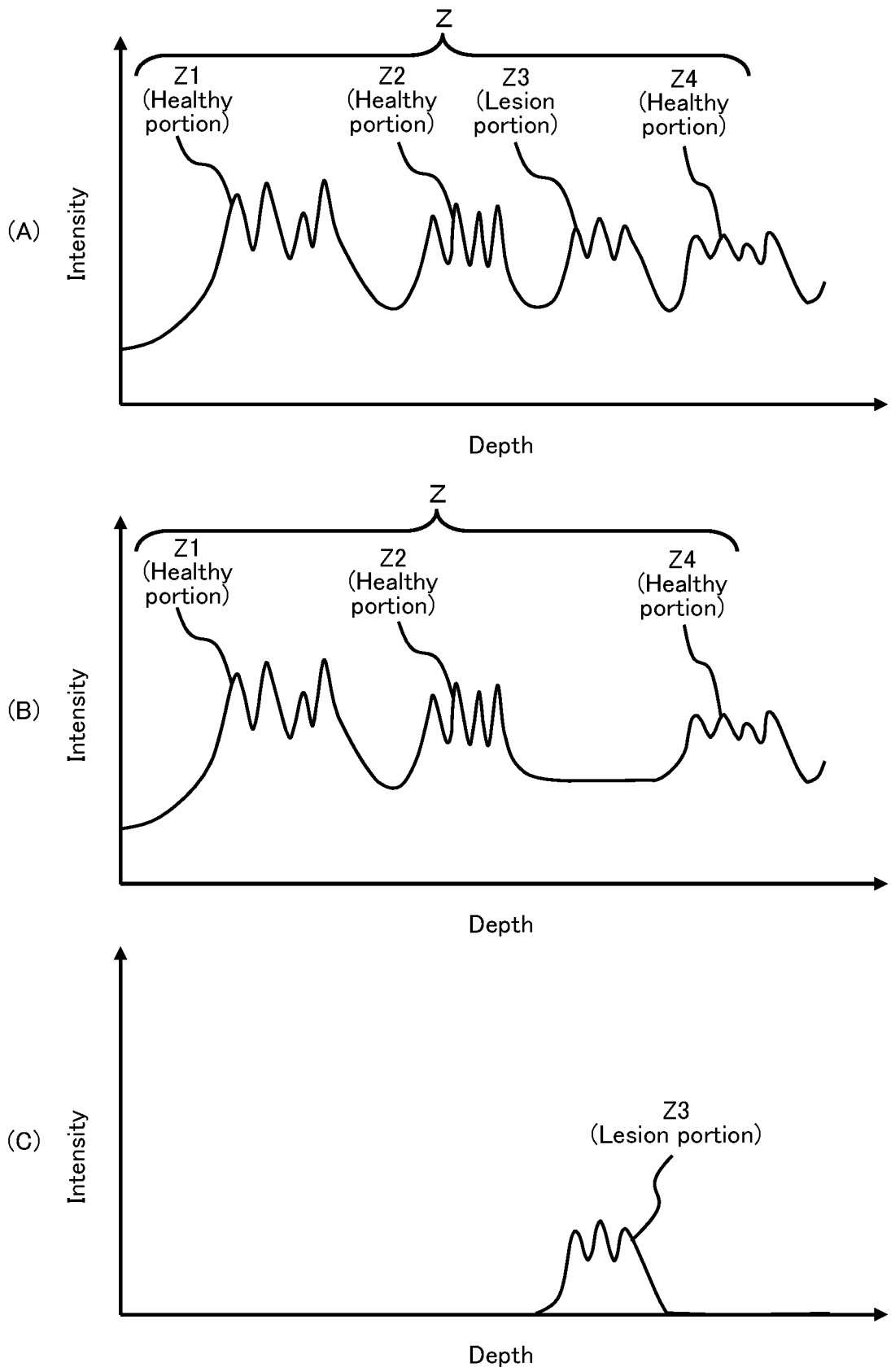
FIG. 8 is a diagram illustrating an example of a waveform of a laser beam obtained by combining a waveform of a laser beam reflected from a therapeutic range and a waveform of a laser beam reflected from a reflecting plate.
Figure 9:
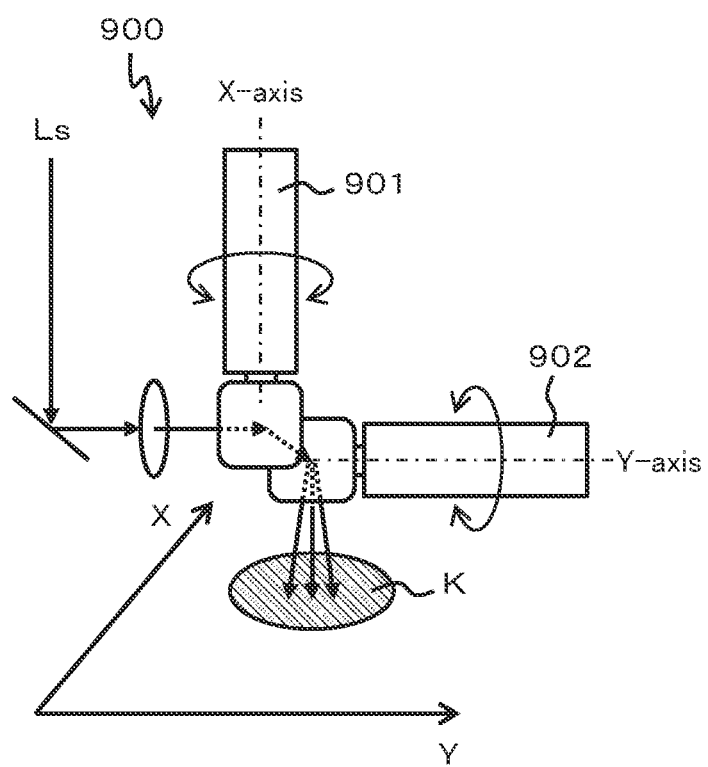
FIG. 9 is a diagram illustrating a laser control mechanism of a conventional laser treatment apparatus.

FIG. 8 is a diagram illustrating an example of a waveform of a laser beam Ls obtained by combining a waveform of a laser beam Ls1 reflected from the therapeutic range K and a waveform of a laser beam Ls2 reflected from a reflecting plate 230. (A) in FIG. 8 illustrates an example of a waveform when a lesion tissue (the affected area Ka) is present, (B) illustrates an example of a waveform when a normal tissue is present, and (C) is a waveform corresponding to a difference between the waveform of the lesion tissue and the waveform of the normal tissue.

As illustrated in FIG. 7, in the laser treatment apparatus 1C, the focal length adjustment mechanism 200 is provided between the scanning device 40 and the lens 50.

The focal length adjustment mechanism 200 includes a third crystal element 210, a wavelength plate 212, a fourth crystal element 214, a reflecting plate 220, a reflecting plate 230, a detector 240, and a storage unit 250.

The third crystal element 210, the wavelength plate 212, and the fourth crystal element 214 are the same elements and wavelength plate as the first crystal element 42, the wavelength plate 44, and the second crystal element 46. That is, the third crystal element 210 and the fourth crystal element 214 are crystal elements (corresponding to transmission media) having an electro-optical effect, and KTN crystals having an electro-optical effect similar to the first and second crystal elements 42 and 46 are used. The refractive index of the crystals of the third and fourth crystal elements 210 and 214 changes when an internal crystal structure changes according to the magnitude of an applied input voltage V (electric field) whereby the focal length of the spot Sp (the depth direction of the skin) of the laser beam Ls can be changed. Moreover, the wavelength plate 212 outputs the incident laser beam Ls by giving a predetermined phase difference to the laser beam Ls.

The reflecting plate 220 transmits a portion of the laser beam Ls output from the fourth crystal element 214 toward the lens 50 and reflects the other portion toward the reflecting plate 230 (a direction orthogonal to the laser beam Ls output from the third crystal element 210). A reflecting plate which is set so that an incident light and a reflection light are equal is used as the reflecting plate 220.

The reflecting plate 230 is provided at a predetermined distance from the reflecting plate 220 and reflects the laser beam Ls received from the reflecting plate 220 toward the detector 240 (one-dot chain line in the drawing). The reflecting plate 230 is provided so as to be movable, and the distance between the reflecting plate 230 and the reflecting plate 220 can be adjusted freely according to the distance between the reflecting plate 220 and the affected area Ka.

Here, the laser beam Ls having passed through the reflecting plate 220 is irradiated to the therapeutic range K of a patient through the lens 50. A portion of the laser beam Ls irradiated to the therapeutic range K is reflected from the skin and is returned to the reflecting plate 220 (a dashed line in the drawing). The laser beam Ls1 reflected from the skin is reflected toward the detector 240 by the reflecting plate 220.

The laser beam Ls of both the laser beam Ls1 reflected from the skin and the laser beam Ls2 reflected from the reflecting plate 230 is incident to the detector 240.

The detector 240 receives the laser beam Ls1 reflected from the skin and the laser beam Ls2 reflected from the reflecting plate 230 and analyzes an interference fringe generated due to an optical path difference between the laser beams Ls1 and Ls2 to detect the depth of the affected area Ka in the therapeutic range K. That is, the detector 240 and a processor (not illustrated) that analyzes an interference fringe generated due to an optical path difference between the laser beams Ls1 and Ls2 perform the function of an interferometer.

As illustrated in (A) in FIG. 8, when the skin has a lesion tissue (diseases, spots, tattoos, or the like), a waveform Z detected by the detector 240 includes a waveform (waveforms Z1, Z2, and Z4 in (A) of FIG. 8) of a light intensity corresponding to a normal tissue and a waveform (Z3 in (A) of FIG. 8) of a light intensity corresponding to a lesion tissue.

As illustrated in (B) in FIG. 8, when the skin does not have a lesion tissue (diseases, spots, tattoos, or the like), the waveform Z detected by the detector 240 includes a waveform (waveforms Z1, Z2, and Z4 in (A) of FIG. 8) of a light intensity corresponding to a normal tissue.

As illustrated in (C) in FIG. 8, the processor (not illustrated) can detect the position or the depth of the lesion tissue by taking a difference between the waveform having the lesion tissue and the waveform which does not have the lesion tissue.

Here, the laser treatment apparatus 1C acquires an interference waveform of the laser beam Ls1 reflected from a healthy skin of the patient and the laser beam Ls2 reflected from the reflecting plate 230 in advance and stores the waveform in the storage unit 250 such as a RAM (Random Access Memory). The processor can determine whether the laser beam Ls1 reflected from the therapeutic range K is the laser beam Ls1 reflected from the affected area Ka (an abnormal area) by comparing an interference waveform of the laser beams Ls1 and Ls2 reflected from the healthy skin stored in the storage unit 250 with an interference waveform of the laser beams Ls1 and Ls2 reflected from the therapeutic range K.

The detector 240 can detect the depth position of the affected area Ka on the basis of the waveform of the laser beam Ls obtained from the interference fringe generated due to the optical path difference between the laser beam Ls1 reflected from the affected area Ka and the laser beam Ls2 having passed through another path.

As described above, in the embodiment, the reflecting plate 230 can change its distance and can collect information in the depth direction of the skin by changing the distance. In the laser treatment apparatus 1C, another beam source (not illustrated) different from the beam source 10 may be provided. In this way, the resolution in the depth direction can be increased by the detector 240 detecting the light intensity of the laser beam output from the other beam source. The reflecting plate 220 may have such a wavelength property that the reflecting plate 220 transmits light from the beam source 10 with substantially no loss and reflects light from another beam source (not illustrated) used for measurement to the reflecting plate 230 with an appropriate reflectivity so as to facilitate measurement.

The laser treatment apparatus 1C can control the input voltage V applied to the third and fourth crystal elements 210 and 214 on the basis of the depth position of the affected area Ka detected by the detector 240 so that the focal length of the spot Sp of the laser beam Ls output from the third and fourth crystal elements 210 and 214 is aligned at the depth position of the affected area Ka. Therefore, the laser treatment apparatus 1C can align the focal length of the spot Sp of the laser beam Ls at the depth position of the affected area Ka and perform treatment of the affected area Ka efficiently.

Particularly, since the laser treatment apparatus 1C controls the focal length of the spot Sp of the laser beam Ls using the third and fourth crystal elements 210 and 214 having an electro-optical effect such as KTN, the laser treatment apparatus 1C can follow high-speed scanning with the laser beam Ls having the wavelength of 1 to 1000 picoseconds and the repetition frequency of 1 kHz to 1 MHz and perform treatment using the laser beam Ls appropriately.

A configuration which includes the reflecting plate 220, the reflecting plate 230, and the detector 240 and in which the detector 240 determines the depth position of the affected area Ka from an interference fringe generated due to an optical path difference between the laser beam Ls1 reflected from the therapeutic range K and the laser beam Ls2 reflected from the reflecting plate 230 corresponds to a depth position detection device of the present disclosure. Although a mechanism (the reflecting plate 220, the reflecting plate 230, and the detector 240) that form an interferometer in a space has been illustrated as an example, an interferometer formed of an optical fiber may be used.

A configuration in which the third crystal element 210, the wavelength plate 212, and the fourth crystal element 214 adjust the focal length of the spot Sp of the laser beam Ls corresponds to a focus adjustment device. The focus adjustment device may be formed of the third crystal element 210 only. Moreover, instead of the third crystal element 210 and the like, the focus adjustment device may be a movable lens, a variable focus lens which uses electric characteristics such as a liquid lens or a liquid crystal lens, or a variable focus lens which uses change in form such as a polymer film or a gel.

A configuration which adjusts the focal length of the laser beam Ls output from the third and fourth crystal elements 210 and 214 on the basis of a depth position detection result of the affected area Ka detected by the detector 240 corresponds to a focal length adjustment mechanism.

As described above, the third embodiment is configured as follows.

(10) The laser treatment apparatus includes the focal length adjustment mechanism 200 that aligns the focal length of the spot Sp of the laser beam Ls output from the scanning device 40 at the depth position of the affected area Ka.

With this configuration, since the laser treatment apparatus 1C can align the focal length of the spot Sp of the laser beam Ls at the depth position of the affected area Ka with the aid of the focal length adjustment mechanism 200, treatment of the affected area Ka can be performed efficiently while suppressing the influence (side effect) on the normal skin.

(11) The focal length adjustment mechanism 200 includes a depth position detection device (a configuration which includes the reflecting plate 220, the reflecting plate 230, and the detector 240 and in which the detector determines a depth position of the affected area Ka from an interference fringe obtained by superimposing the waveform of the laser beam Ls1 reflected from the therapeutic range K and the laser beam Ls2 reflected from the reflecting plate 230) that detects the depth position of the affected area Ka and the third and fourth crystal elements 210 and 214 (the focus adjustment device) that adjust the focal length of the spot Sp of the laser beam Ls on the basis of the depth position detection result of the affected area Ka detected by the depth position detection device.

With this configuration, in the laser treatment apparatus 1C, since the focal length of the spot Sp of the laser beam Ls output from the third and fourth crystal elements 210 and 214 is adjusted according to the depth position of the affected area Ka detected by the depth position detection device, treatment of the affected area Ka at a predetermined depth position can be performed while suppressing an influence (side effect) on a normal skin.

(12) The laser treatment apparatus includes the storage unit 250 that stores a detection result of a normal area detected by the depth position detection device (the reflecting plate 220, the reflecting plate 230, and the detector 240), and the depth position detection device detects the depth position of the affected area Ka on the basis of the result of comparison with the normal are detection result stored in the storage unit 250.

With this configuration, the detector 240 can determine the affected area Ka and detect the depth position of the affected area Ka appropriately by comparing the detection result of the normal area and the detection result of the affected area Ka.

The beam source 10 may output a linearly polarized laser beam.

While examples of the embodiments of the present disclosure have been described, all the embodiments may be combined with each other and arbitrary two or more embodiments may be combined with each other.

The present disclosure is not limited to including all components of the above embodiments, some of the components of the above embodiments may be replaced with components of the other embodiments, and the components of the above embodiments may be replaced with the components of the other components.

The components of some of the above-described embodiments may be added to, removed from, or replaced with the components of the other embodiments.

What is claimed is:

1. A laser treatment apparatus that is configured to irradiate a laser beam to an affected area to treat the affected area, the laser treatment apparatus comprising:
   a beam source device that is configured to output a laser beam;
   a polarization varying device that includes a crystal element configured to change a polarization direction of the laser beam output by the beam source device;
   a scanning device that is configured to scan a therapeutic range including the affected area with the laser beam by irradiating the laser beam to the therapeutic range, wherein the scanning device has a transmission medium that changes an output direction of a laser beam according to an applied voltage, and the transmission medium includes a first transmission medium that is configured to change an output direction of a laser beam polarized in a first direction by the polarization varying device according to an applied voltage;
   a polarizer that is provided upstream of the first transmission medium in a path of the laser beam and is configured to transmit a laser beam having a polarization component that is either the same or orthogonal to that of the laser beam passing through the first transmission medium; and
   a controller that controls the polarization varying device to adjust the polarization direction of the laser beam output from the polarization varying device based on a polarization direction of the polarizer.

2. The laser treatment apparatus according to claim 1, wherein the transmission medium further includes a second transmission medium that is configured to change an output direction of a laser beam polarized in a second direction orthogonal to the first direction according to an applied voltage.

3. The laser treatment apparatus according to claim 2, further comprising
   a detector that is configured to detect the laser beam output by the beam source device, wherein
   the controller is configured to control the polarization direction of the laser beam polarized by the polarization varying device on the basis of a detection result of the laser beam detected by the detector.

4. The laser treatment apparatus according to claim 3, wherein:
   the polarizer is provided on an incidence side of the laser beam incident to the detector,
   the detector is provided on an upstream side of the first transmission medium in the path of the laser beam, and
   the controller is configured to control the polarization direction of the laser beam polarized by the polarization varying device on the basis of a detection result of the laser beam detected by the detector via the polarizer.

5. The laser treatment apparatus according to claim 3, wherein:
   the detector is provided on a downstream side of the first transmission medium in the path of the laser beam, and
   the controller is configured to control polarization of the laser beam polarized by the polarization varying device on the basis of a detection result of the laser beam detected by the detector.

6. The laser treatment apparatus according to claim 1, wherein:
   the transmission medium further includes a second transmission medium that is configured to change an output direction of the laser beam polarized in a second direction orthogonal to the first direction according to an applied voltage, and
   the scanning device includes a wavelength plate that is provided between the first transmission medium and the second transmission medium in the path of the laser beam and is configured to output the laser beam from the first transmission medium by giving a predetermined phase difference to the laser beam.

7. The laser treatment apparatus according to claim 1, further comprising
   a focal length adjustment mechanism that is configured to align a focal length of the laser beam output from the scanning device to a depth position of the affected area.

8. The laser treatment apparatus according to claim 7, wherein
the focal length adjustment mechanism includes:
a depth position detection device that is configured to detect a depth position of the affected area; and
a focus adjustment device that is configured to adjust a focal length of the laser beam on the basis of a detection result of the depth position of the affected area detected by the depth position detection device.

9. The laser treatment apparatus according to claim 8, further comprising:
a storage unit that is configured to store a detection result of a normal area detected by the depth position detection device, wherein
the depth position detection device is configured to detect the depth position of the affected area on the basis of a result of comparison with the detection result of the normal area stored in the storage unit.

10. The laser treatment apparatus according to claim 7, wherein
the focus adjustment device includes a transmission medium that is provided on a downstream side of the scanning device in a path of the laser beam and changes a focal length of the laser beam according to an applied voltage, and
the focal length adjustment mechanism is configured to control a voltage applied to the transmission medium on the basis of a detection result of the depth position of the affected area detected by the depth position detection device and change the focal length of the laser beam.

11. The laser treatment apparatus according to claim 1, wherein
the transmission medium is a crystal element.

12. The laser treatment apparatus according to claim 11, wherein
the crystal element of the transmission medium is at least one of LN crystals, LT crystals, or KTN crystals.

13. The laser treatment apparatus according to claim 1, further comprising
a light guiding component formed of an optical fiber that is configured to guide the laser beam output from the beam source device to the scanning device and maintain polarization.

14. The laser treatment apparatus according to claim 1, further comprising
an optical axis adjustment mechanism that is configured to adjust an optical axis of the laser beam, wherein:
the optical axis adjustment mechanism includes a detector that is configured to detect the laser beam, an optical axis adjuster that is configured to adjust the optical axis of the laser beam, and an adjuster controller that is configured to control the optical axis adjuster, and
the adjuster controller is configured to control the optical axis adjuster according to a light intensity of the laser beam detected by the detector.

15. The laser treatment apparatus according to claim 1, wherein
the beam source device is configured to output a laser beam having a repetition frequency of 1 kHz to 10 MHz with a pulse width of 1 to 1000 picoseconds.

* * * * *